United States Patent
Sigmon, Jr.

(10) Patent No.: US 9,468,498 B2
(45) Date of Patent: Oct. 18, 2016

(54) MAGNETIC ACTIVATION OF MONOPOLAR AND BIPOLAR DEVICES

(71) Applicant: COOK MEDICAL TECHNOLOGIES LLC, Bloomington, IN (US)

(72) Inventor: John C. Sigmon, Jr., Greensboro, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 844 days.

(21) Appl. No.: 13/722,520

(22) Filed: Dec. 20, 2012

(65) Prior Publication Data

US 2014/0180280 A1   Jun. 26, 2014

(51) Int. Cl.
| | |
|---|---|
| *A61B 18/18* | (2006.01) |
| *A61B 18/14* | (2006.01) |
| *H01R 11/30* | (2006.01) |
| *A61B 18/00* | (2006.01) |

(52) U.S. Cl.
CPC ........... *A61B 18/18* (2013.01); *A61B 18/1492* (2013.01); *H01R 11/30* (2013.01); *A61B 2018/00178* (2013.01); *A61B 2018/00535* (2013.01); *A61B 2018/00553* (2013.01); *A61B 2018/00601* (2013.01); *A61B 2018/144* (2013.01); *H01R 2201/12* (2013.01)

(58) Field of Classification Search
CPC .............. A61B 18/1492; A61B 18/18; A61B 2018/00178; A61B 2018/00535; A61B 2018/00553; A61B 2018/00601; A61B 2018/144

See application file for complete search history.

(56) References Cited

U.S. PATENT DOCUMENTS

| | | | |
|---|---|---|---|
| 4,112,941 A | 9/1978 | Larimore | |
| 4,211,456 A | 7/1980 | Sears | |
| 5,813,996 A | 9/1998 | St. Germain et al. | |
| 5,984,920 A | 11/1999 | Steinbach | |
| 6,827,718 B2 * | 12/2004 | Hutchins | A61B 18/1492 128/898 |
| 7,121,827 B2 | 10/2006 | Lampert | |
| 7,182,604 B2 | 2/2007 | Ehr et al. | |
| 7,442,042 B1 | 10/2008 | Lewis | |
| 7,722,358 B2 * | 5/2010 | Chatterjee | G06F 3/03543 439/38 |
| 7,722,412 B2 | 5/2010 | Ehr et al. | |
| 7,935,130 B2 | 5/2011 | Williams | |
| 7,963,773 B2 | 6/2011 | Palli et al. | |
| 9,011,428 B2 * | 4/2015 | Nguyen | A61B 18/1402 606/41 |

(Continued)

OTHER PUBLICATIONS

European Patent Office, International Search Report of PCT/US2013/076071, Mailed on Mar. 28, 2014, 4 pages, Netherlands.

*Primary Examiner* — Amanda Patton
(74) *Attorney, Agent, or Firm* — Brinks Gilson & Lione

(57) ABSTRACT

A system for providing current to perform a surgical procedure includes an electrosurgical device having a conductive cutting wire and a power source with a power cord providing current to the cutting wire from a power source. The power cord and device are connected via a magnetic connection. The magnetic connection includes a device housing coupled to a cord housing, where a magnetic post is received in a recess for mechanically and electrically connecting the cutting wire and an active wire of the power cord. The recess and the magnetic post can be coaxial, with the axes being perpendicular to longitudinal axes of the device housing and the cord housing so that the connection can withstand a force exerted along the longitudinal axis, but a sufficient force transverse to the longitudinal axes and along the axes of the recess and the post can de-couple the magnetic connection.

19 Claims, 6 Drawing Sheets

(56) References Cited

U.S. PATENT DOCUMENTS

| | | |
|---|---|---|
| 2003/0216723 A1 | 11/2003 | Shinmura et al. |
| 2008/0311765 A1 | 12/2008 | Chatterjee et al. |
| 2011/0087217 A1 | 4/2011 | Yates et al. |
| 2012/0100729 A1 | 4/2012 | Edidin et al. |
| 2012/0148195 A1 | 6/2012 | Umeno |
| 2012/0226273 A1 | 9/2012 | Nguyen et al. |
| 2012/0310265 A1 | 12/2012 | Martinez |

* cited by examiner

MAGNETIC ACTIVATION OF MONOPOLAR AND BIPOLAR DEVICES

BACKGROUND

1. Field of the Invention

The present embodiments relate generally to a system for providing electrosurgery using electrosurgical devices and, more particularly, to an electrosurgical device having a magnetic connection for transmitting power to the electrosurgical device from a power source.

2. Description of Related Art

The use of electrosurgical devices to perform medical procedures on a patient is common in the medical field. One type of electrosurgical device is a sphincterotome. Sphincterotomes are commonly used to incise or cut a sphincter of a patient. A sphincter is a generally circular muscle that generally maintains constriction of a natural body passage or orifice. A surgeon can operate a sphincterotome to cannulate various ductal systems that include sphincters, such as the biliary duct.

Common sphincterotomes includes structure for navigating through the patient's body to a location where cannulation of the sphincter is desired. The sphincterotome includes a cutting wire that is exposed at the distal end of the device. The cutting wire can be energized to provide heat to the wire for cutting and cauterizing the surgical area for cannulation. As such, common sphincterotomes are electrically connected to a power source for providing the electrical energy to the cutting wire.

Sphincterotomes can be either monopolar or bipolar. In a monopolar device, the active electrical path is provided by the device, with the patient's body providing the return path through an electrosurgical pad or other known method. In a bipolar device, the return path is carried back through the device via a return wire. Both monopolar and bipolar devices are common in the art and require no further discussion.

Whether in a monopolar or bipolar device, the electrical wires receiving and providing power are connected to a power source for providing power to the device. The power source is generally a separate component from the device, where various devices or device types can be attached thereto. Thus, the electrosurgical device requires a connection to the power source.

One type of connection to the power source is in the form of a universal pin. The universal pin can be disposed either on the device or from the power source. The pin is received in a corresponding receptacle at either the device or the power source. This pin and receptacle connection is generally maintained through friction, snap fit, or other mechanical type connection. However, this type of connection is susceptible to breaking in the event that a force is applied transverse to the axis of the connection, which can be costly to repair or replace in the event that the pin is broken.

Another type of connection is in the form of a banana plug. Banana plugs can be used to connect wires with a pin-shaped receptacle similar to the above. However, installing the banana plug to the wires can be time consuming, and similarly suffers from the risk of breaking as described above. In the event that the banana plug is damaged, replacement of the banana plug can be costly and time consuming during a medical procedure.

Yet another type of connection can be in the form of a coaxial cable connection. Coaxial connections are known in the art, where one end of a wire can be mechanically coupled to a corresponding receptacle. This connection can withstand forces applied thereto generally better than a pin-style connection, but suffers from the inability to become unseated in the event of a sufficient force acting against it, which can lead to damage to the electrosurgical device or connected power source if it does not become un-coupled.

With respect to bipolar connections, the above described connections generally require two connections: one for the active wire and another for the receiving wire. Connecting two wires can require additional time to make the connections relative to a single connection. A monopolar device generally requires only the single active wire to be connected to the power source. However, the monopolar device requires the additional use of an electrical pad connected to the patient to provide the return path.

Sphincterotomes are generally single use devices, being disposed of after use by the surgeon. Thus, there is a need for a connection between the sphincterotome and the power source that is easy to attach, while likewise being easy to detach in the event of a force applied to it that limits damage to the connection.

SUMMARY

A system for providing an electrical current during surgery is provided, the system comprising: an elongate electrosurgical device having a distal end and proximal end and a longitudinal device axis extending therebetween; a conductive cutting wire mounted to the device and extending along the longitudinal axis, the conductive cutting wire having an exposed cutting portion at the distal end; a device housing at the proximal end of the device, the device housing at least partially covering the conductive cutting wire mounted therein; an elongate cord having proximal and distal ends and a longitudinal cord axis therebetween with an active wire therein for transferring power from a power source; a cord housing at the distal end of the elongate cord, the cord housing covering at least a portion of the active wire; a magnetic connection between the device housing and the cord housing, the magnetic connection comprising both a mechanical and electrical connection; a recess of the magnetic connection extending generally transverse to the longitudinal axes of the device housing and the cord housing, the recess comprising a recessed magnetic surface; a magnetic post of the magnetic connection extending generally transverse to the longitudinal axes of the device housing and the cord housing and sized to correspond to the shape of the recess; wherein the magnetic surface is electrically connected to one of the conductive wire or the active wire; wherein the magnetic post is electrically connected to the other of the conductive wire or the active wire; wherein the magnetic post contacts the magnetic surface and is magnetically and electrically coupled thereto for transferring power from the active wire to the conductive wire; and wherein the magnetic post is received in the recess perpendicular to the longitudinal axes of the device housing and the cord housing.

In another form, the system further comprises a device return wire extending along the electrosurgical device and a power source return wire extending along the power cord.

In another form, the system further comprises a second recess and a second magnetic post, and wherein the second recess includes a second recessed magnetic surface, and the device return wire and power source return wire are coupled via a magnetic connection between the second magnetic post and the second recessed magnetic surface.

In another form, the electrosurgical device is a sphincterotome.

In another form, the electrosurgical device includes a handle portion, the handle portion includes an actuating ring, and the actuating ring is a portion of the device housing.

In another form, the conductive cutting wire includes a curved portion extending around a portion of the actuating ring.

In another form, the device housing includes a stepped portion, the cord housing includes a head portion, and the head portion is received in the stepped portion.

In another form, the head portion and stepped portion have a generally racetrack shape.

In another form, the conductive cutting wire terminates at the distal end of the electrosurgical device.

In another form, the device return wire is coupled to a conductive portion disposed at the distal end of the electrosurgical device.

In another form, the device housing includes the recess and the cord housing includes the magnetic post.

In another form, the magnetic post and the recess have a generally cylindrical shape.

In one form, a method for connecting an electrosurgical device to a power source is provided, the method comprising: providing an electrosurgical device having a proximal end and a distal end, a longitudinal axis extending therebetween, and a conductive cutting wire extending generally along the longitudinal axis; wherein the device includes a housing at the proximal end and the housing includes a recess therein having an axis that is generally transverse to the longitudinal axis of the device, and the recess includes a recessed magnetic surface; wherein the recessed magnetic surface is electrically connected to the conductive cutting wire; providing a power cord having an active wire extending along a longitudinal axis of the cord; wherein the power cord includes a cord housing at a distal end thereof; wherein the cord housing includes a magnetic post extending therefrom generally transverse to the to the longitudinal axis of the cord; aligning the axes of the magnetic post and the recess; aligning the longitudinal axes of the device housing and the cord housing; inserting the magnetic post into the recess; contacting the magnetic post with the recessed magnetic surface to create a magnetic connection therebetween.

In another form, the axes of the magnetic post and the recess are aligned coaxially.

In another form, the cord housing includes two magnetic posts and the device housing includes two recesses, and the two magnetic posts are inserted into the two recesses.

In another form, the cord housing includes a head portion, the device housing includes a stepped portion sized for receiving the head portion, and the method further comprises the step of inserting the head portion into the stepped portion.

In another form, the device includes a return wire therein, the power cord includes a return wire therein, and the return wires are electrically connected through a connection between one of the magnetic posts and one of the recessed surfaces.

In one form, an elongate electrosurgical device is provided comprising: a tubular body having a proximal and distal end and a longitudinal axis therebetween; a handle portion coupled to the proximal end of the tubular body, the handle portion having a longitudinal axis therealong; a housing of the handle portion at a proximal end thereof; a recess extending into the housing, the recess having an axis that is generally perpendicular to the longitudinal axis of the handle portion; a recessed magnetic surface disposed within the recess; a cutting wire electrically connected to the recessed magnetic surface and extending through the handle portion and the tubular body to the distal end thereof; and wherein the recess is sized to receive a magnetic post having a shape corresponding to the recess for electrically connecting the cutting wire to an active wire electrically connected to the magnetic post.

In another form, the housing includes a stepped portion therein sized to receive a head portion of a cord housing having the magnetic post extending therefrom.

In another form, the device further comprises: a second recess having a second recessed magnetic surface therein; a conductive return wire electrically connected to the second recessed magnetic surface and extending within the handle portion and the tubular body to the distal end thereof; and wherein the conductive return wire is electrically connected to the cutting wire.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1:
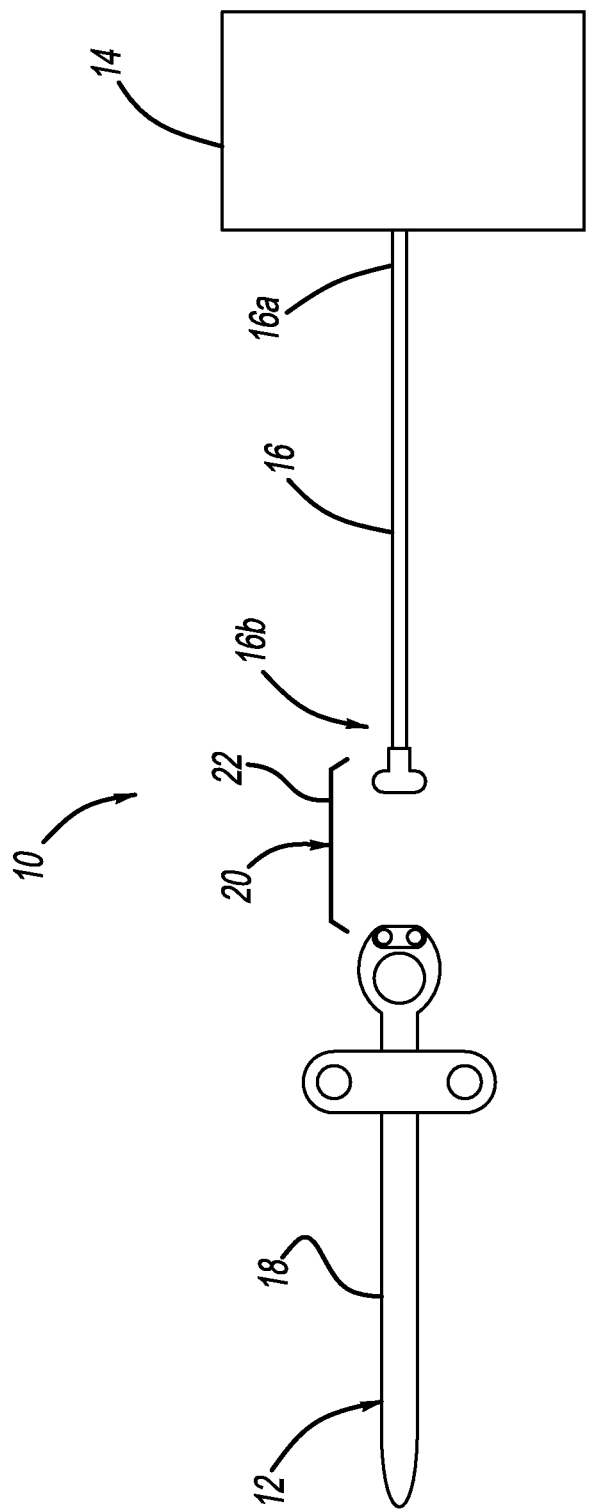
FIG. 1 is a schematic view of an electrosurgical system having an electrosurgical device, a power source, and an electrical cord connecting the device and the power source.

Referring now to the drawings, FIG. 1 illustrates an electrosurgical system 10 including an electrosurgical device 12, a power source 14, and an electrical cord or power cord 16 connecting the device 12 and the power source 14. In one form, the electrosurgical device 12 is in the form of a sphincterotome 18.

The electrical cord or power cord 16 can generally include a proximal end 16a that is connected to the power source 14 and a distal end 16b that is connected to the sphincterotome 18. The cord 16 can be connected to the sphincterotome 18 via an electromechanical connection 20. The electromechanical connection 20 can be in the form of a magnetic connection 22, which will be further described below.

Figure 2:
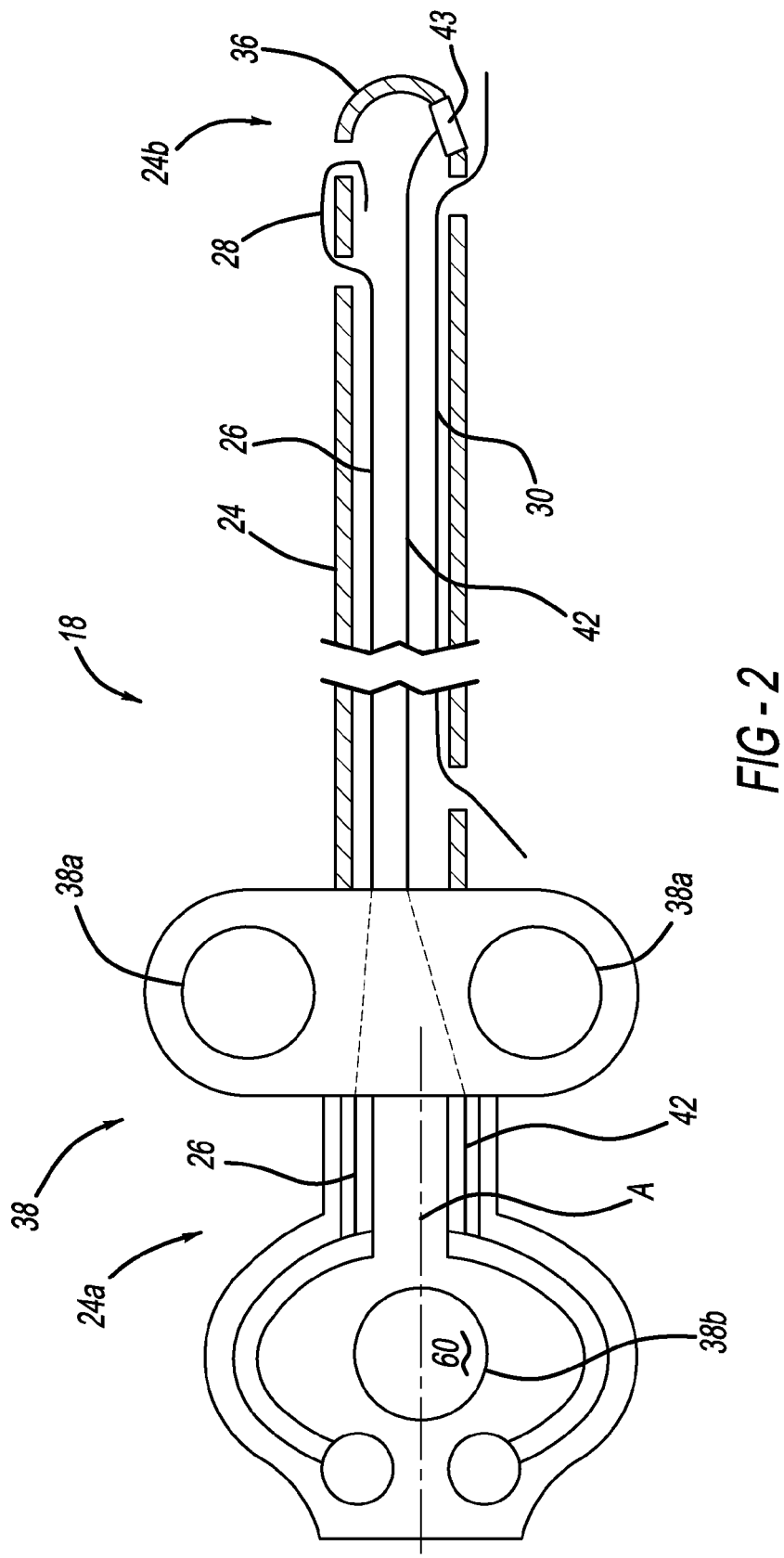
FIG. 2 is a partial cross-sectional schematic view of the electrosurgical device having a handle portion and a tubular body with a cutting wire and a return wire therein.

With reference now to FIG. 2, the sphincterotome 18 includes a tubular body 24 having a proximal end 24a and a distal end 24b. The tubular body 24 includes a cutting wire 26 extending therethrough, where a cutting portion 28 of the cutting wire 26 extends outside of the tubular body 24 at the distal end 24b. The tubular body 24 can also include a guidewire 30 extending therealong, with the guidewire 30 extending outside of the tubular body 24 at the distal end 24b. As known in the art, the tubular body 24 can also include a cutting wire lumen (not shown) and a guidewire lumen (not shown) through which the cutting wire 26 and guidewire 30 extend, respectively. It will be appreciated that FIG. 2 is a schematic representation, and the cutting wire 26 and guidewire 30 do not generally share a common lumen.

The sphincterotome 18 can also include a distal tip 36 at the distal end 24b of the tubular body 24 that can be manipulated and bent by actuating a handle portion 38 disposed at the proximal end 24a as is known in the art. The handle portion 38 includes a pair of gripping rings 38a that assist in gripping the handle portion 38, as well as an actuating ring 38b that is coupled to the cutting wire 26. Actuating the handle portion 38 includes pulling on the actuating ring 38b, which puts the cutting wire 26 in tension in a manner known in the art. Putting the cutting wire 26 in tension will cause the distal tip 36 to bend and arc, where the cutting portion 28 of the cutting wire will form a secant with the arced distal tip 36. The cutting portion 28 of the cutting wire 26 can then cut and cauterize tissue at the adjacent anatomical area, as is known in the art, to cannulate a sphincter.

The handle portion 38 has a generally longitudinal length with a longitudinal axis A that can generally correspond to the longitudinal axis of the tubular body 24 of the sphincterotome 18. The handle portion 38 includes one half of the electromechanical connection 20 between the sphincterotome 18 and the power source cord 16, which will be described in further detail below.

The power source 14 can be a standard power source 14 for use in electrosurgical procedures such as sphincterotomy or the like. The power source 14 can be configured to supply an electrical current to the sphincterotome 18, wherein the resistive properties of the cutting wire 26 will result in the cutting wire 26 becoming heated, as is known in the art, to cut and cauterize adjacent tissue.

Figure 3:
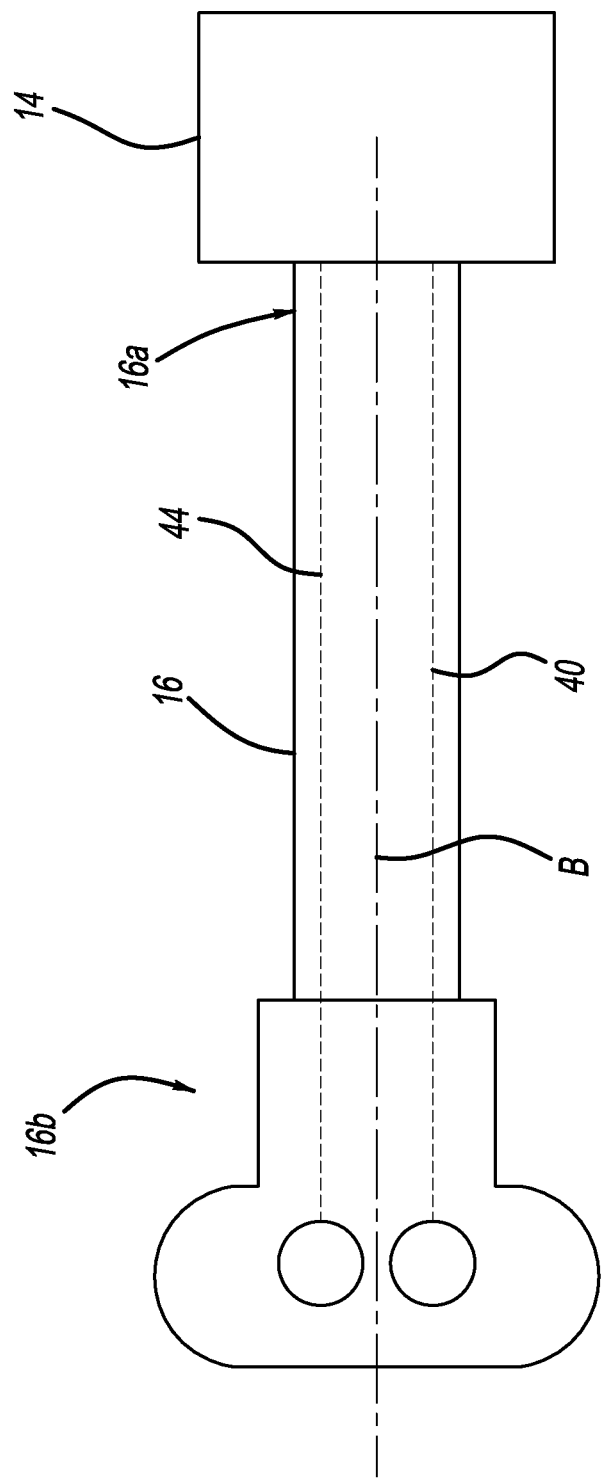
FIG. 3 is a schematic view of the electrical cord having an active wire and a return wire therein.

With reference to FIG. 3, the power cord 16 can extend from the power source 14 for connection to the device 12 via the electromechanical connection 20. The power cord 16 can be integral with the power source 14, or can be coupled to the power source 14 via a typical plug-in type connection (not shown) or the like, as is known in the art. The power cord 16 is generally flexible in nature, and includes an active wire 40 extending therethrough and insulated via known wire insulation methods. The active wire 40 carries the current from the power source 14 to the cutting wire 26 via the electromechanical connection 20 with the sphincterotome 18. The power cord 16 includes a proximal end 16a, which is connected the power source 14, a distal end 16b, and a longitudinal axis B extending therebetween. The distal end 16b comprises one half of the electromechanical connection 20 for coupling with the other half of the connection 20 of the sphincterotome 18, further described below.

The sphincterotome 18 can include a return wire 42 and the power cord 16 can include a return wire 44 for completing the electrical circuit in a bipolar configuration. In the case of the sphincterotome 18, the return wire 42 can be coupled to a conductive portion 43 disposed at the distal tip 36 in a manner known in the art and shown schematically in FIG. 2. In a monopolar configuration, the sphincterotome 18 and power cord 16 will include the cutting wire 26 and the active wire 40, respectively, but no return wire. In the monopolar configuration, the circuit is completed through the patient via an electrical pad or connection connected thereon and further connected to a negative terminal of the power source 14, or to a ground. In the bipolar configuration, the circuit is completed through the patient's tissue, which contacts the conductive portion 43 and returned through the return wire 42. As mentioned above, FIG. 2 is a schematic representation, and the return wire 42 will generally extend through a dedicated lumen (not shown) and will not share a common lumen with the cutting wire 26 and the guidewire 30.

Figure 4:
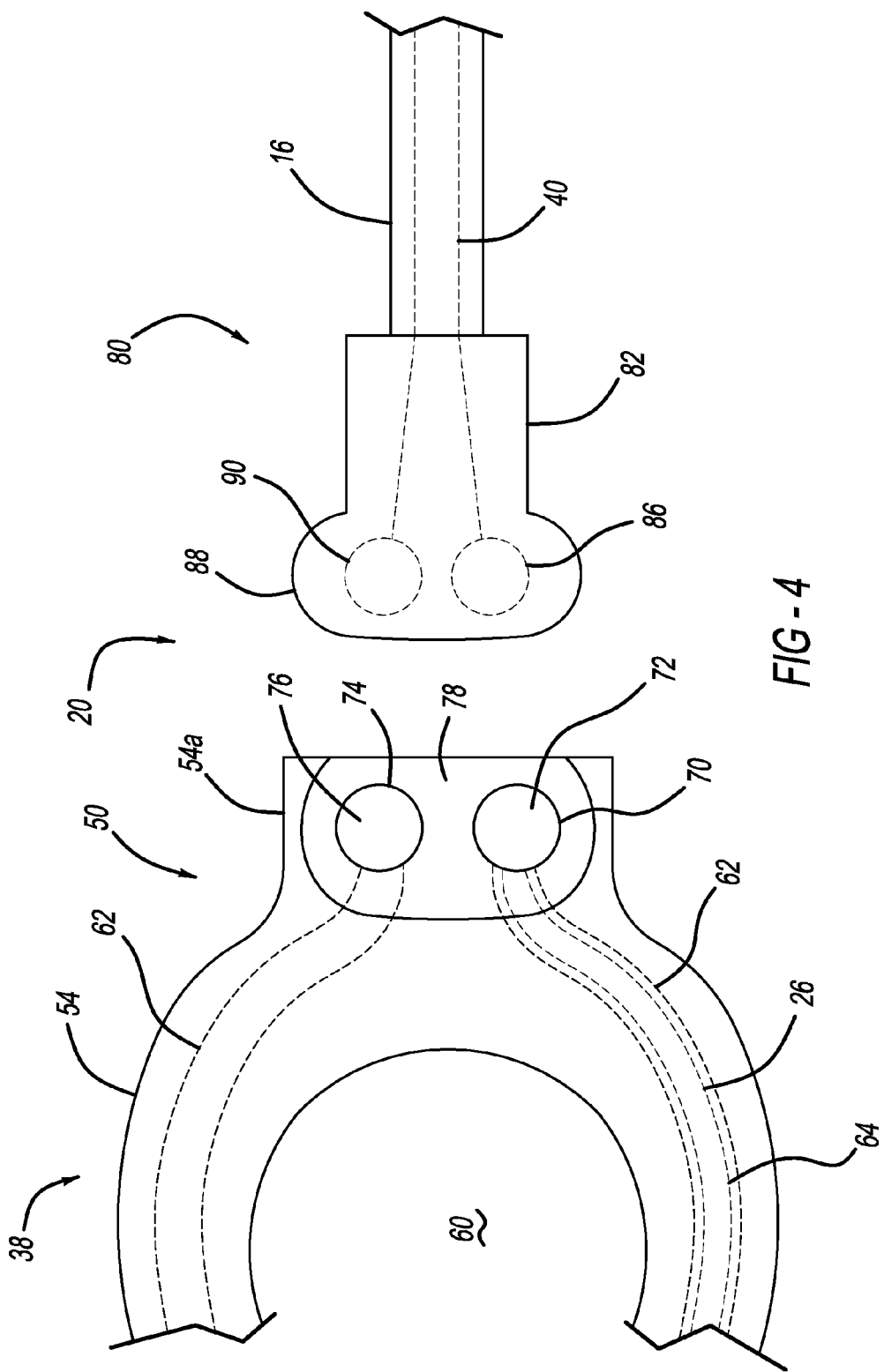
FIG. 4 is a plan view of an electromechanical connection between a device housing of the electrosurgical device and a power cord housing of the electrical cord.
Figure 5:
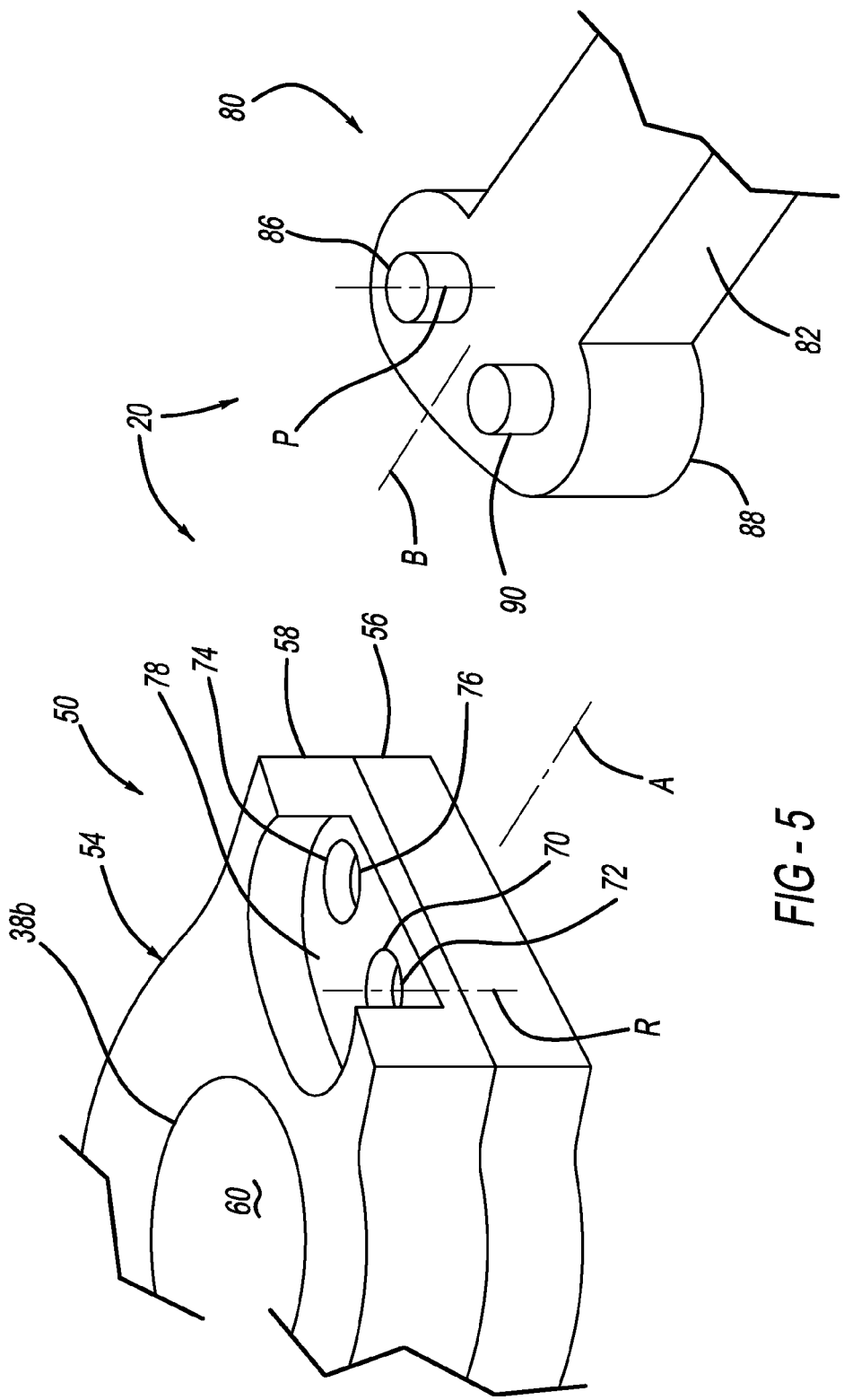
FIG. 5 is an isometric view of the device housing and power cord housing.
Figure 6:
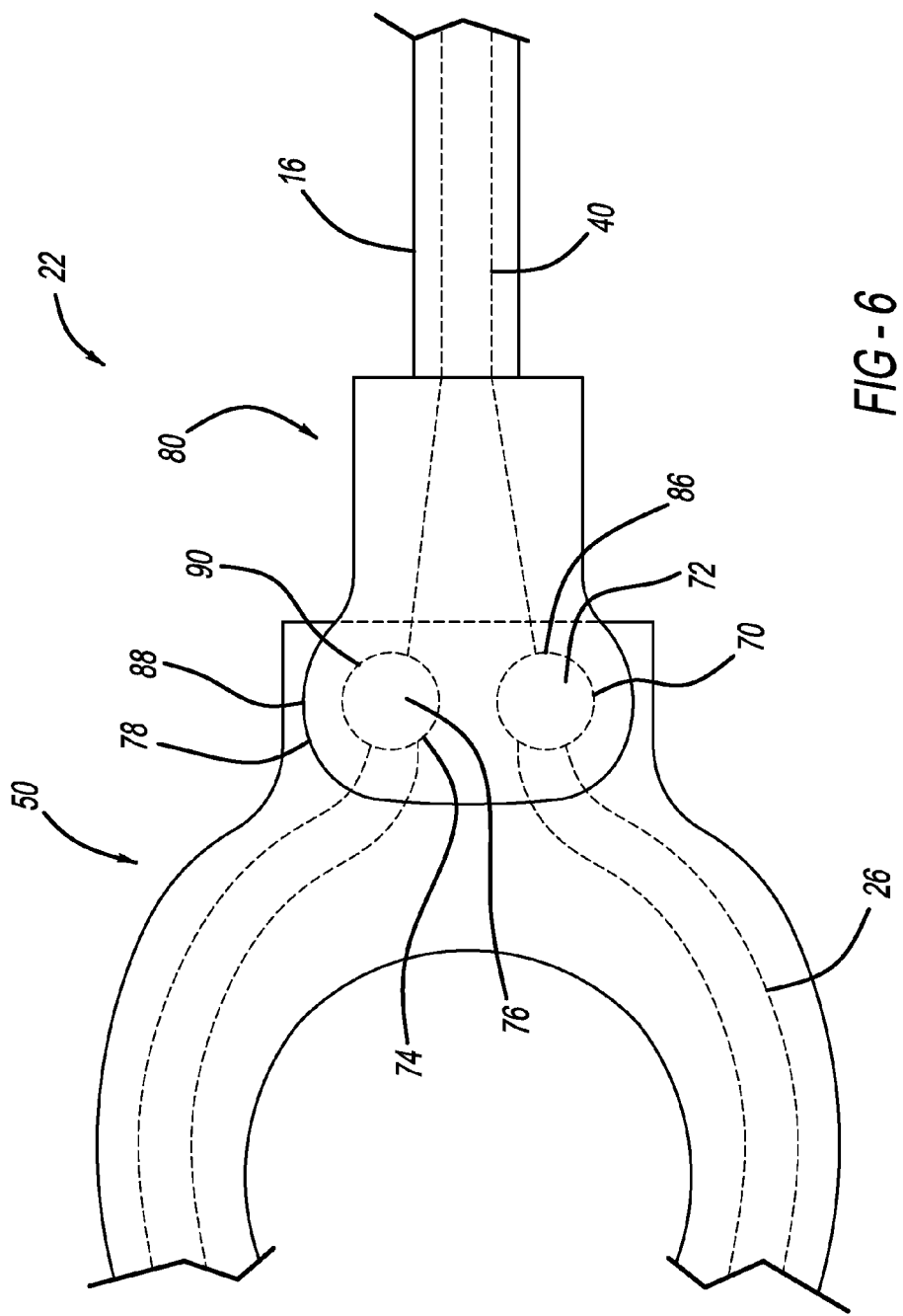
FIG. 6 is a plan view of the device housing coupled to the power cord housing.

With reference to FIGS. 4-6, the electromechanical connection 20 can be in the form of the magnetic connection 22 and can include a first housing or device housing 50 coupled to the handle portion 38 of the sphincterotome 18 and a second housing or power cord housing 80 coupled to the distal end 16b of the power cord 16. The device housing 50 and power cord housing 80 can be coupled together via cooperating structure discussed in further detail below.

In one form, the device housing 50 can include a device housing body 54 having a proximal end 54a. The body 54 can have a generally two-piece configuration comprising a base member 56 and a lid member 58. The base member 56 and lid member 58 can have generally similar outer profiles, so that when they are mated together via a mechanical or adhesive connection, the base member 56 and lid member 58 will combine to create the housing body 54.

As shown, in one form, the device housing 50 can comprise the actuating ring 38b of the handle portion 38 with an actuating ring hole 60 extending through the device housing 50.

The base member 56 can include at least one recessed channel 62 extending in a generally longitudinal direction from the proximal end 54a of the housing body 54 and along the handle portion 38 of the sphincterotome 18. The channel 62 can have a curved shape to account for the shape of the device housing 50 and handle portion 38. For example, as shown in FIG. 4, the channel 62 can extend about the hole 60 of the device housing 50 when the housing 50 comprises the actuating ring 38b of the handle portion 38.

The cutting wire 26 can be disposed within the channel 62 so that it will run from the distal tip 36 to the proximal end 54a of the housing body 54. In one form, the cutting wire 26 can include a flat ribbon shaped curved portion 64, where the curved portion 64 extends about the hole 60.

As shown in FIG. 5, the proximal end 54a of the housing body 54 can include a generally cylindrical shaped opening or recess 70 having an axis R that is generally transverse and perpendicular to the longitudinal axis A of the device 12 and the handle portion 38. The recess 70 can include a recessed magnetic mating surface 72 therein. The magnetic mating surface 72 is electrically connected to the cutting wire 26 by way of soldering or other known methods.

The magnetic mating surface 72 can have properties sufficient for being magnetically coupled to a corresponding magnet having the opposite polarity. The magnetic mating surface 72 can also have properties sufficient for transmitting an electric current therethrough, so that when coupled to a corresponding electrically conductive magnet, the magnetic surface 72 will transfer the current to the cutting wire 26.

In the case of a bipolar configuration for the sphincterotome 18, the device housing 50 can include a second recess 74 and a second recessed magnetic surface 76 having a configuration similar to the recess 70 and mating surface 72. However, rather than carrying the current and load from the power source 14, the second recessed surface 76 will carry the current of the return path from the return wire 42.

In addition to the recess 70 and the mating surface 72, the housing 50 can also include a stepped portion 78. The stepped portion 78 can be flat and shaped to mate with a corresponding portion of a power cord housing 80, which will be further described below. In one form, the stepped portion 78 can have a generally "racetrack" shape.

With further reference to FIG. 5, the power cord housing 80 can be disposed at the distal end 16b of the power cord 16 that extends from the power source 14. The power cord housing 80 can include a cord housing body 82. The cord housing 80 can also include a magnetic post 86 having a generally cylindrical shape that corresponds to the cylindrical shape of the recess 70 in the device housing 50. The magnetic post 86 has an axis P that is generally transverse and perpendicular to the longitudinal axis B of the power cord 16 and the cord housing 80.

The housing body 82 can include a head portion 88 at the distal end thereof. The head portion 88 can have a shape corresponding to the stepped portion 78 of the device housing 50. In one form, the head portion 88 can have a generally "racetrack" shape so that the head portion 88 can become seated onto the stepped portion 78 of the device housing 50.

The magnetic post 86 extends from the head portion 88, so that when the head portion 88 is received on the stepped portion 78 of the device housing 50, the magnetic post 86 can be received in the recess 70 of the device housing 50. When the device housing 50 and cord housing 80 are coupled in this manner, the magnetic post 86 will become magnetically coupled to the recessed magnetic surface 72 of the device housing 50 to form the magnetic connection 22. This magnetic connection 22 can withstand a separation force applied thereto that is below a predetermined threshold level, while becoming disconnected in response to a separation force that is greater than the threshold level. The magnetic connection 22 will also transmit an electrical current therethough, so that that a current from the power source 14 through the power cord 16 will be passed on to the sphincterotome 18.

In a bipolar device 12, the cord housing 80 can include a second magnetic post 90 similar to the magnetic post 86 described above. Rather than provide the active current, the second magnetic post 90 will provide the connection for the return path in a manner known in the art.

Having described the general structure of the electrosurgical system 10, including the sphincterotome 18, the power source 14, and the connection 20 therebetween, the general use of the system 10 will now be described.

As described above, the sphincterotome 18 is generally a single use device 12, such that the device 12 can be discarded after use. For a particular medical procedure, a new sphincterotome 18 can be provided for connection to the system 10 and the power source 14.

To connect the sphincterotome 18 to the system 10, the surgeon can simply locate the device housing 50 having the recess 70 and the recessed magnetic surface 72. In one form, the device housing 50 is integral with the handle portion 38, where the device housing 50 includes the actuating ring 38b of the handle portion 38. In this form, the surgeon can locate the device housing 50 by locating the proximal end of the handle portion 38.

The power source 14 having the power cord 16 can be provided for connection to the sphincterotome 18. The surgeon can locate the power cord 16 and the distal end 16b thereof, which includes the cord housing 80. The surgeon can locate the head portion 88 of the cord housing 80, which includes the magnetic posts 86 and 90 described above.

With reference to FIG. 6, the surgeon can manipulate the head portion 88 to align the magnetic posts 86 and 90 with the recesses 70 and 74 in the device housing 50. The surgeon can next insert the magnetic posts 86 and 90 into the recesses 70 and 74 of the device housing 50. The magnetic properties of the magnetic posts 86 and 90 and the recessed magnetic surfaces 72 and 76 will operate to magnetically couple the posts 86 and 90 and recessed surfaces 72 and 76, thereby creating the magnetic connection 22 between the device housing 50 and the cord housing 80.

With the insertion of the magnetic posts 86 and 90, the head portion 88 is also inserted into the device housing 50 at the stepped portion 78, so that the head portion 88 is received therein. The coupling of the head portion 88 and the stepped portion 78 creates a mechanical connection in the longitudinal direction corresponding to the power cord 16 and the sphincterotome 18.

Thus, by coupling the two housings 50 and 80, the surgeon can create a longitudinal mechanical connection that can withstand a longitudinal force exerted thereon by way of pushing or pulling on the cord 16 or sphincterotome 18. Additionally, the magnetic connection 22, being aligned transverse to the longitudinal direction, creates a connection that can withstand a force acting in a direction transverse to the longitudinal axis of the sphincterotome 18 and the power cord 16. Put another way, the axes R and P can be generally coaxially aligned with each other, with the axes A and B being generally parallel, where axes R and P are generally perpendicular to axes A and B.

However, the magnetic connection that is arranged to withstand a transverse force is also arranged to become de-coupled in the event of a sufficient transverse force. For example, if the surgeon or another person makes inadvertent contact with the magnetic connection in the transverse direction, the connection can become de-coupled, allowing the cord 16 to fall away from the sphincterotome 18 while limiting trauma to the patient caused by the inadvertent contact. This is in contrast to a longitudinally aligned pin-type connection, where a transverse force could result in the sphincterotome 18 becoming misaligned or torqued within the patient's body, or in the pin breaking, resulting in costly repair or replacement.

In the event the connection 22 becomes de-coupled, the surgeon can simply re-locate the cord 16 and make the connection 22 again. The magnetic nature of the connection 22 allows for a fast and easy manner of connecting the sphincterotome 18 to the power cord 16 repeatedly, if necessary.

Similarly, absent an inadvertent force against the connection, when the surgeon has completed the medical procedure using the sphincterotome 18, the surgeon can simply grasp the connection 22 and de-couple the magnetic connection 22, removing the head portion 88 of the cord housing 80 from the stepped portion 78 of the device housing 50, thereby removing the magnetic posts 86 and 90 from the recesses 70 and 74.

The use of the sphincterotome 18 to perform cannulation of various sphincters within the body has been referred to generally above. Additional detail regarding the use of the sphincterotome 18 can be found in United States Patent Application Publication No. 2009/0043259, filed Aug. 8, 2007 and published Feb. 12, 2009, which is hereby incorporated by reference in its entirety. Further detail regarding the use and structure of the bipolar configuration of the sphincterotome 18 can be found in U.S. Pat. No. 5,035,696, filed Feb. 2, 1990 and issued Jul. 30, 1991, which is hereby incorporated by reference in its entirety.

While the above description refers to the device housing 50 having the recesses 70 and 74, and the cord housing 80 having the magnetic posts 86 and 90 for being received in the recesses 70 and 74, it will be appreciated that the opposite configuration could also be used, where the device housing 50 includes the posts 86 and 90 and the power cord 16 includes the recesses 70 and 74.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for providing an electrical current during surgery, the system comprising:
    an elongate electrosurgical device having a distal end and proximal end and a longitudinal device axis extending therebetween;
    a conductive cutting wire mounted to the device and extending along the longitudinal axis, the conductive cutting wire having an exposed cutting portion at the distal end;
    a device housing at the proximal end of the device, the device housing at least partially covering the conductive cutting wire mounted therein;
    an elongate cord having proximal and distal ends and a longitudinal cord axis therebetween with an active wire therein for transferring power from a power source;
    a cord housing at the distal end of the elongate cord, the cord housing covering at least a portion of the active wire;
    a magnetic connection between the device housing and the cord housing, the magnetic connection comprising both a mechanical and electrical connection;
    a recess of the magnetic connection extending generally transverse to the longitudinal axes of the device housing and the cord housing, the recess comprising a recessed magnetic surface;
    a magnetic post of the magnetic connection extending generally transverse to the longitudinal axes of the device housing and the cord housing and sized to correspond to the shape of the recess;
    wherein the magnetic surface is electrically connected to one of the conductive wire or the active wire;
    wherein the magnetic post is electrically connected to the other of the conductive wire or the active wire;
    wherein the magnetic post contacts the magnetic surface and is magnetically and electrically coupled thereto for transferring power from the active wire to the conductive wire;
    wherein the magnetic post is received in the recess perpendicular to the longitudinal axes of the device housing and the cord housing;
    wherein the electrosurgical device includes a handle portion, the handle portion includes an actuating ring and gripping rings, and the actuating ring is a portion of the device housing and disposed proximally relative to gripping rings;
    wherein the magnetic connection is disposed in the actuating ring.

2. The system of claim 1 further comprising a device return wire extending along the electrosurgical device and a power source return wire extending along the power cord.

3. The system of claim 2 further comprising a second recess and a second magnetic post, and wherein the second recess includes a second recessed magnetic surface, and the device return wire and power source return wire are coupled via a magnetic connection between the second magnetic post and the second recessed magnetic surface.

4. The system of claim 1, wherein the electrosurgical device is a sphincterotome.

5. The system of claim 1, wherein the conductive cutting wire extends through the handle portion and includes a curved portion extending around a portion of the actuating ring and terminating at the magnetic connection within the actuating ring.

6. The system of claim 1, wherein the device housing includes a stepped portion, the cord housing includes a head portion, and the head portion is received in the stepped portion.

7. The system of claim 6, wherein the head portion and stepped portion have a generally elongate and curved shape, wherein the elongate and curved shape is wider in a direction transverse to the longitudinal axis than in a direction along the longitudinal axis.

8. The system of claim 1, wherein the conductive cutting wire terminates at the distal end of the electrosurgical device.

9. The system of claim 2, wherein the device return wire is coupled to a conductive portion disposed at the distal end of the electrosurgical device.

10. The system of claim 1, wherein the device housing includes the recess and the cord housing includes the magnetic post.

11. The system of claim 1, wherein the magnetic post and the recess have a generally cylindrical shape.

12. A method for connecting an electrosurgical device to a power source, the method comprising:
    providing an electrosurgical device having a proximal end and a distal end, a longitudinal axis extending therebetween, and a conductive cutting wire extending generally along the longitudinal axis;
    wherein the device includes a housing at the proximal end, the housing including a handle portion having an actuator ring disposed proximally from at least one gripping ring, and the housing includes a recess therein having an axis that is generally transverse to the longitudinal axis of the device, and the recess includes a recessed magnetic surface, wherein the recess is disposed in the actuating ring;
    wherein the recessed magnetic surface is electrically connected to the conductive cutting wire;
    providing a power cord having an active wire extending along a longitudinal axis of the cord;
    wherein the power cord includes a cord housing at a distal end thereof;
    wherein the cord housing includes a magnetic post extending therefrom generally transverse to the to the longitudinal axis of the cord;
    aligning the axes of the magnetic post and the recess;
    aligning the longitudinal axes of the device housing and the cord housing;
    inserting the magnetic post into the recess;
    contacting the magnetic post with the recessed magnetic surface to create a magnetic connection therebetween.

13. The method of claim 12, wherein the axes of the magnetic post and the recess are aligned coaxially.

14. The method of claim 12, wherein the cord housing includes two magnetic posts and the device housing includes two recesses, and the two magnetic posts are inserted into the two recesses.

15. The method of claim 12, wherein the cord housing includes a head portion, the device housing includes a stepped portion sized for receiving the head portion, and the method further comprises the step of inserting the head portion into the stepped portion.

16. The method of claim 14, wherein the device includes a return wire therein, the power cord includes a return wire therein, and the return wires are electrically connected through a connection between one of the magnetic posts and one of the recessed surfaces.

17. An elongate electrosurgical device comprising:

a tubular body having a proximal and distal end and a longitudinal axis therebetween;

a handle portion coupled to the proximal end of the tubular body, the handle portion having a longitudinal axis therealong;

a housing of the handle portion at a proximal end thereof, the housing including an actuating ring of the handle portion disposed proximally from at least one gripping ring of the handle portion;

a recess extending into the actuating ring, the recess having an axis that is generally perpendicular to the longitudinal axis of the handle portion;

a recessed magnetic surface disposed within the recess;

a cutting wire electrically connected to the recessed magnetic surface and extending through the handle portion and the tubular body to the distal end thereof; and wherein the recess is sized to receive a magnetic post having a shape corresponding to the recess for electrically connecting the cutting wire to an active wire electrically connected to the magnetic post.

18. The device of claim 17, wherein the housing includes a stepped portion therein sized to receive a head portion of a cord housing having the magnetic post extending therefrom.

19. The device of claim 17 further comprising;

a second recess having a second recessed magnetic surface therein;

a conductive return wire electrically connected to the second recessed magnetic surface and extending within the handle portion and the tubular body to the distal end thereof; and wherein the conductive return wire is electrically connected to the cutting wire.

* * * * *